US010842687B2

(12) United States Patent
Barnes et al.

(10) Patent No.: US 10,842,687 B2
(45) Date of Patent: Nov. 24, 2020

(54) PANT STRUCTURE WITH EFFICIENTLY MANUFACTURED AND AESTHETICALLY PLEASING REAR LEG EDGE PROFILE

(71) Applicant: The Procter & Gamble Company, Cincinnati, OH (US)

(72) Inventors: Jillian Marie Barnes, Madeira, OH (US); Ronald Joseph Zink, Blue Ash, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 777 days.

(21) Appl. No.: 14/837,359

(22) Filed: Aug. 27, 2015

(65) Prior Publication Data
US 2016/0058627 A1    Mar. 3, 2016

Related U.S. Application Data

(60) Provisional application No. 62/042,387, filed on Aug. 27, 2014.

(51) Int. Cl.
*A61F 13/15*    (2006.01)
*A61F 13/20*    (2006.01)
(Continued)

(52) U.S. Cl.
CPC .. *A61F 13/49011* (2013.01); *A61F 13/15203* (2013.01); *A61F 13/15593* (2013.01);
(Continued)

(58) Field of Classification Search
CPC ............... A61F 13/15593; A61F 13/49; A61F 13/49011; A61F 13/4902; A61F 13/4963;
(Continued)

(56) References Cited

U.S. PATENT DOCUMENTS 4,919,738 A    4/1990    Ball et al.
5,340,648 A    8/1994    Rollins et al.
(Continued)

FOREIGN PATENT DOCUMENTS

EP    2659870 A1    11/2013
JP    4971109    6/2009
(Continued)

OTHER PUBLICATIONS

PCT International Search Report, dated Oct. 12, 2015 (11 pages).

*Primary Examiner* — Michele M Kidwell
(74) *Attorney, Agent, or Firm* — Daniel S. Albrecht; William E. Gallagher

(57) ABSTRACT

A disposable absorbent pant having a front belt portion and a rear belt portion is disclosed. The front and rear belt portions are joined at side seams and the rear belt portion has a greater length than the front belt portion. A lower edge of the rear belt portion forms at least in part edges of left and right leg openings to the rear of the side seams. The rear belt portion includes first and second layers of nonwoven web material sandwiching a plurality of laterally extending and laterally pre-strained elastic strands, disposed below the side seams. A first of the plurality of elastic strands differs from a second of the plurality of elastic strands by one or more of amount of pre-strain, tensile modulus, decitex, and combinations thereof.

20 Claims, 11 Drawing Sheets

(51) Int. Cl.
  *A61F 13/49* (2006.01)
  *A61F 13/496* (2006.01)
  *A61F 13/56* (2006.01)

(52) U.S. Cl.
  CPC .......... *A61F 13/49* (2013.01); *A61F 13/4902* (2013.01); *A61F 13/4906* (2013.01); *A61F 13/4963* (2013.01); *A61F 13/5655* (2013.01); *A61F 2013/15365* (2013.01); *A61F 2013/15406* (2013.01); *A61F 2013/4908* (2013.01); *A61F 2013/49025* (2013.01); *A61F 2013/49026* (2013.01); *A61F 2013/49028* (2013.01); *A61F 2013/49068* (2013.01); *A61F 2013/49088* (2013.01)

(58) Field of Classification Search
  CPC .. A61F 2013/15365; A61F 2013/15406; A61F 2013/49025; A61F 2013/49026; A61F 2013/49028; A61F 13/15203; A61F 13/4906; A61F 13/5655; A61F 13/49088; A61F 13/4908
  See application file for complete search history.

(56) References Cited

U.S. PATENT DOCUMENTS

| | | | |
|---|---|---|---|
| 5,382,400 A | 1/1995 | Pike et al. | |
| 5,418,045 A | 5/1995 | Pike et al. | |
| 5,501,756 A | 3/1996 | Rollins et al. | |
| 5,507,909 A | 4/1996 | Rollins et al. | |
| 5,622,722 A | 4/1997 | Stokes et al. | |
| 5,707,468 A | 1/1998 | Arnold et al. | |
| 6,077,375 A | 6/2000 | Kwok | |
| 6,200,635 B1 | 3/2001 | Kwok | |
| 6,235,137 B1 | 5/2001 | Van Eperen et al. | |
| 6,361,634 B1 | 3/2002 | White et al. | |
| 6,454,989 B1 | 9/2002 | Neely et al. | |
| 6,520,237 B1 | 2/2003 | Bolyard et al. | |
| 6,561,430 B2 | 5/2003 | Ou | |
| 6,582,518 B2 | 6/2003 | Riney | |
| 6,610,161 B2 | 8/2003 | Erdman | |
| 6,613,146 B2 | 9/2003 | Bolyard | |
| 6,626,879 B1 * | 9/2003 | Ashton | A61F 13/496 604/385.01 |
| 6,632,385 B2 | 10/2003 | Kauschke et al. | |
| 6,632,386 B2 | 10/2003 | Shelley et al. | |
| 6,645,569 B2 | 11/2003 | Cramer et al. | |
| 6,652,693 B2 | 11/2003 | Burriss et al. | |
| 6,719,846 B2 | 4/2004 | Nakamura et al. | |
| 6,737,102 B1 | 5/2004 | Saidman et al. | |
| 6,803,103 B2 | 10/2004 | Kauschke et al. | |
| 6,863,933 B2 | 3/2005 | Cramer et al. | |
| 7,112,621 B2 | 9/2006 | Rohrbaugh et al. | |
| 7,291,239 B2 | 11/2007 | Polanco et al. | |
| 7,858,544 B2 | 12/2010 | Turi et al. | |
| 8,186,296 B2 | 5/2012 | Brown et al. | |
| 8,308,706 B2 | 11/2012 | Rukae | |
| 8,445,744 B2 | 5/2013 | Autran et al. | |
| 8,475,424 B2 | 7/2013 | Fujimoto et al. | |
| 8,728,051 B2 | 5/2014 | Lu et al. | |
| 9,039,669 B1 | 5/2015 | LaVon et al. | |
| 2005/0008839 A1 | 1/2005 | Cramer et al. | |
| 2006/0030831 A1 | 2/2006 | Matsuda et al. | |
| 2013/0211363 A1 | 8/2013 | LaVon et al. | |
| 2013/0324957 A1 | 12/2013 | Gassner et al. | |

FOREIGN PATENT DOCUMENTS

| | | |
|---|---|---|
| JP | 2011-115304 A | 6/2011 |
| JP | 2012135519 | 7/2012 |
| JP | 2012148069 | 8/2012 |
| JP | 2013048728 | 3/2013 |

* cited by examiner

PANT STRUCTURE WITH EFFICIENTLY MANUFACTURED AND AESTHETICALLY PLEASING REAR LEG EDGE PROFILE

BACKGROUND OF THE INVENTION

In order to maintain or grow their market share, manufacturers of disposable absorbent articles such as disposable diapers and absorbent pants must continue to discover and develop improvements to materials, components and features that affect aspects such as containment, absorbency, comfort, fit and appearance. Absorbent pants are manufactured in smaller sizes to be used as, e.g., pull-on diapers and toilet training pants for young children, and in larger sizes to be used as, e.g., undergarments for persons suffering from incontinence.

A particular type of absorbent pant design currently marketed is sometimes called the "balloon" pant. The balloon pant design usually includes a central absorbent chassis and an elastic belt. The elastic belt is usually relatively wide (in the longitudinal direction) and elastically stretchable in the lateral direction. It entirely encircles the wearer's waist, and thereby covers a relatively large amount of the wearer's skin, and also makes up a relatively large portion of the visible outside surfaces of the pant. The central chassis portion is typically joined to the inside of the belt in the front, wraps under the wearer's lower torso between the legs, and is joined to the inside of the belt in the rear. The belt is often formed of two layers of nonwoven web sandwiching one or more elastic members such as a plurality of laterally-oriented strands or strips of elastomeric material, or a section of elastomeric film or elastomeric nonwoven. It is common among such designs that, in manufacture, the elastic member(s) are sandwiched between the nonwoven web layers in a strained condition. Upon completion of manufacture and allowance of the belt with sandwiched elastic member(s) to assume a relaxed condition, the elastic member(s) contract laterally toward their unstrained lengths. This causes the nonwoven web layers to form gathers that take the form of visible rugosities in the belt.

The belt structure may be formed of separately formed front and rear portions, joined at seams along the side/hip areas. It may be desired in some circumstances that the front portion have less length (in the vertical direction relative a standing wearer) than the rear portion, to provide a leg opening that is higher in front to permit easier body movement and/or provide less opportunity for rubbing and chafing at the front leg openings. Conversely, it may be desired that the rear portion have greater length, to provide greater coverage of the wearer's buttocks.

When such front and rear portions of the belt are joined at side seams, however, the leg openings will have step profiles at the seams where the longer rear belt portion meets the shorter front portion. If a compensating modification is not made, the step profiles may present an awkward or unsightly appearance when the pant is worn. Portions of the material along the step profiles adjacent the edges of the leg openings in the rear may flip or curl and present a ragged, unfinished or haphazard appearance.

One way in which to address this problem is to cut a curved leg cutout profile into at least the rear portion of the belt structure during manufacture of the pant. Such cutting, however, adds cost and complexity to manufacturing, by creating a need for the design, fabrication and operation of efficient cutting equipment for the manufacturing line, a system for removal of the cutoff scrap from the line equipment and plant environment, and a system and/or procedure for either recycling the scrap or disposing of it as waste.

The balloon pant design provides for certain efficiencies in manufacture, and it is believed that the design may gain popularity. Consequently, a need for alternatives in the design of a belt structure that address these issues is presented.

DETAILED DESCRIPTION OF THE INVENTION

Figure 1:
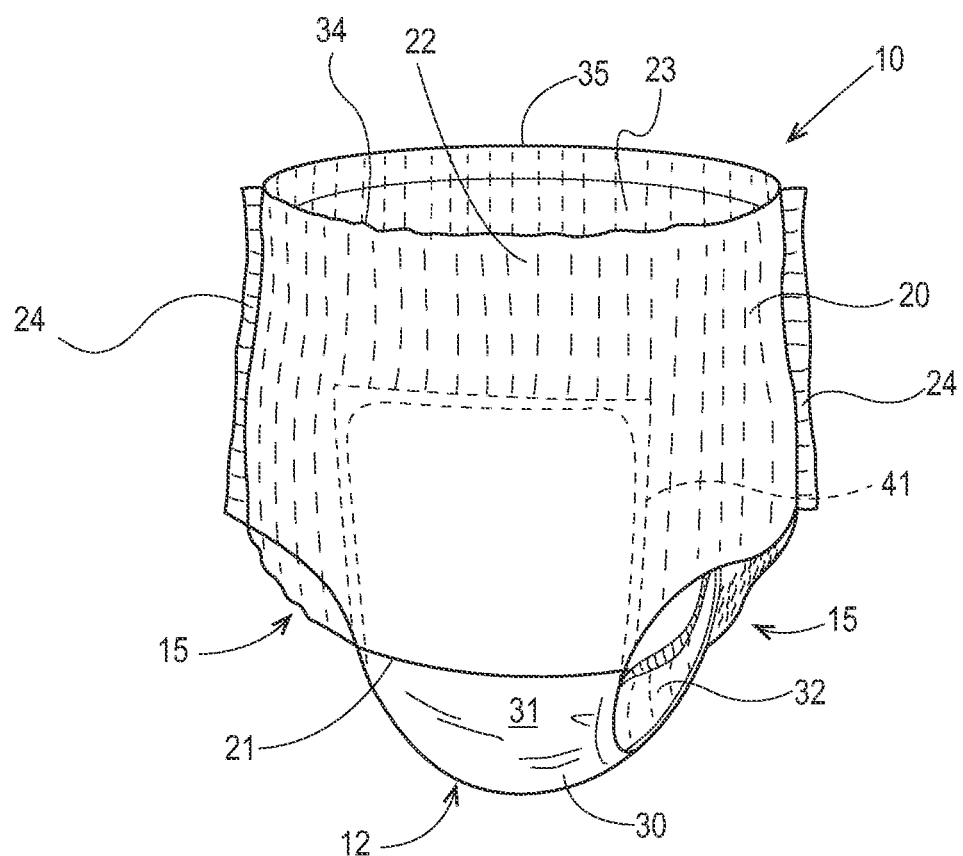
FIG. 1 is a front perspective view of an example of a balloon pant.

"Cross direction" (CD)—with respect to the making of a nonwoven web material, the nonwoven material itself, a laminate thereof, or an article in which the material is a component, refers to the direction along the material substantially perpendicular to the direction of forward travel of the material through the manufacturing line in which the material and/or article is manufactured.

Throughout the present description, a material or composite of materials is considered to be "elastic" or "elastomeric" if, when a biasing force is applied to the material, the material or composite can be extended to an elongated length of at least 150% of its original relaxed length (i.e. can extend at least 50%), without rupture or breakage which substantially damages the material or composite, and when the force is removed from the material or composite, the material or composite recovers at least 40% of such elongation. In various examples, when the force is removed from an elastically extensible material, the material or composite may recover at least 60% or even at least 80% of its elongation.

"Elongation," used herein to quantify and express an amount of longitudinal strain imparted to an elastic strand, means: [(strained length of the strand−length of the strand before straining)/(length of the strand before straining)]× 100%. Where the term "pre-strain" is used to refer to elongation imparted to an elastic strand during manufacture of a belt structure or pant, it refers to elongation, expressed in the same manner.

"Film" means a macroscopically continuous skin-like or membrane-like layer of material formed of one or more polymers. "Film" is distinguished from "nonwoven web" or "nonwoven" in that the latter has a form consisting of a web-like structure of consolidated but predominately individually distinct fibers. "Lateral"—with respect to a pant and its wearer, refers to the direction generally perpendicular to the wearer's standing height, or the horizontal direction when the wearer is standing.

"Longitudinal"—with respect to a pant and its wearer, refers to the direction generally parallel to the wearer's standing height, or the vertical direction when the wearer is standing. "Longitudinal" is also the direction generally parallel to a line extending from the midpoint of the front waist edge, between the leg openings, to the midpoint of the rear waist edge of the pant, when the pant structure is separated at the side/hip seams and laid out unfolded, extended and flat.

With respect to a pant, positional terms such as "lower," "lowest", "above," "below," "bottom," etc., and forms thereof, are expressed with respect to the vertically lowest extent (at the crotch region) and uppermost extent (at the waist edges) of the pant structure along a vertical direction, when worn by a standing wearer. With respect to a precursor structure to the pant, the lowest portions are proximate the lateral axis (axis 100 depicted in the figures) and the highest portions are proximate the waist edges.

"Machine direction" (MD)—with respect to the making of a nonwoven web material, the nonwoven material itself, or a laminate thereof, refers to the direction along the material or laminate substantially parallel to the direction of forward travel of the material or laminate through the manufacturing line in which the material or laminate is manufactured.

"Machine direction bias," with respect to the fibers forming a nonwoven web, means that a majority of the fibers, as situated in the web and unstretched, have lengths with machine direction vector components that are greater than their cross direction vector components.

A "nonwoven" is a manufactured sheet or web of directionally or randomly oriented fibers which are first deposited and accumulated onto a moving surface (such as a conveyor belt) and then consolidated and bonded together by friction, cohesion, adhesion or one or more patterns of bonds and bond impressions created through localized compression and/or application of pressure, heat, ultrasonic or heating energy, or a combination thereof. The term does not include fabrics which are woven, knitted, or stitch-bonded with yarns or filaments. The fibers may be of natural and/or man-made origin and may be staple and/or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwovens can be formed by many processes including but not limited to meltblowing, spunbonding, spunmelting, solvent spinning, electrospinning, carding, film fibrillation, melt-film fibrillation, airlaying, dry-laying, wetlaying with staple fibers, and combinations of these processes as known in the art. The basis weight of a nonwovens is usually expressed in grams per square meter (gsm). "Preexisting," with respect to a pattern of apertures on a nonwoven web, the nonwoven web forming a layer of a laminate, means that the pattern of apertures was formed on the nonwoven web prior to the incorporation of the nonwoven web into the laminate.

"Z-direction," with respect to a web, means generally orthogonal or perpendicular to the plane approximated by the web along the machine and cross direction dimensions.

Although examples of the structure of the invention are described herein as used to form the belt of a balloon-type absorbent pant, it will be appreciated that examples may be used to form other components of pants, diapers, other wearable articles, and other products as well.

Figure 2:
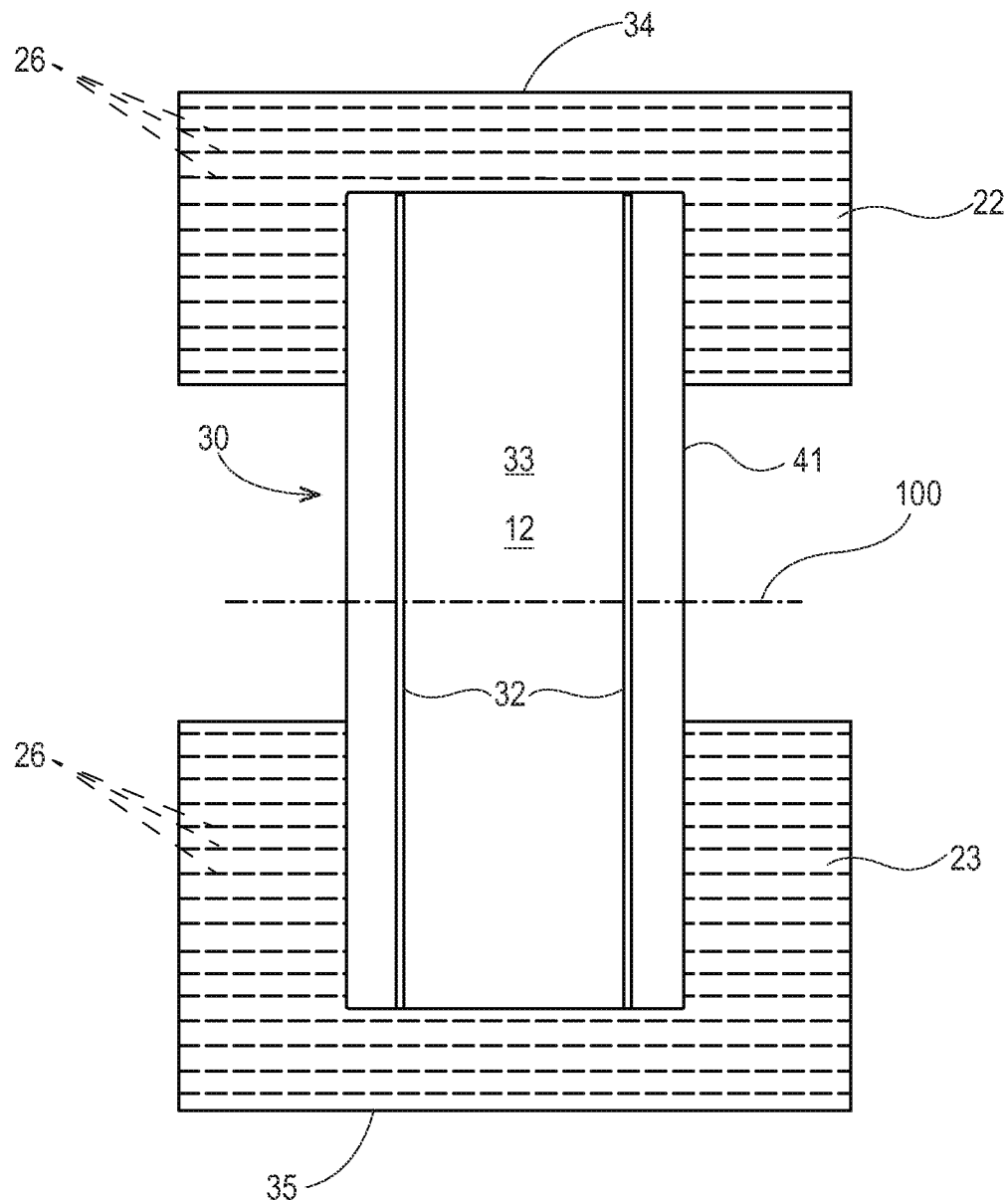
FIG. 2 is a schematic plan view of a balloon pant precursor structure, prior to joining of the front and rear belt portions at side seams, wearer-facing surfaces facing the viewer.

FIG. 1 depicts an example of balloon-type absorbent pant 10. FIG. 2 depicts the precursor structure of the pant in an open configuration laid out flat and stretched out laterally against elastic-induced contraction, wearer-facing surfaces facing the viewer, prior to final assembly in which front belt portion 22 is joined to rear belt portion 23 at seams 24. To form pant 10, the precursor structure may be folded at or about lateral axis 100 (located at the longitudinal midpoint of the precursor structure) with the topsheet 33 facing inward, and the longitudinal edges of the front 22 and rear 23 belt portions may be joined at seams 24, forming a pant structure having leg openings 15, front waist edge 34 and rear waist edge 35.

The pant structure may include a belt 20 and a central chassis 30. Central chassis 30 may include any combination of components found in the absorbent structures of disposable diapers and absorbent pants, including but not limited to a liquid impermeable backsheet 31 formed at least in part of liquid impermeable web material, a liquid permeable topsheet 33, an absorbent core structure (not specifically shown), and elasticized barrier cuffs 32. Examples and descriptions of components and configurations of a central chassis may be found in U.S. Pat. App. Pub. No. US 2013/0211355, wherein the chassis described includes components and features that may be included in central chassis 30. In the example shown in FIG. 1, the front portion of belt 20 stops short of the crotch region 12 of the pant, at lower edge 21. Central chassis 30 may overlie front and rear belt portions 22, 23 to the inside (wearer-facing side) thereof. The outer perimeter 41 of the central chassis 30 may be defined by the outer perimeter of the liquid impermeable web material.

Figure 3:
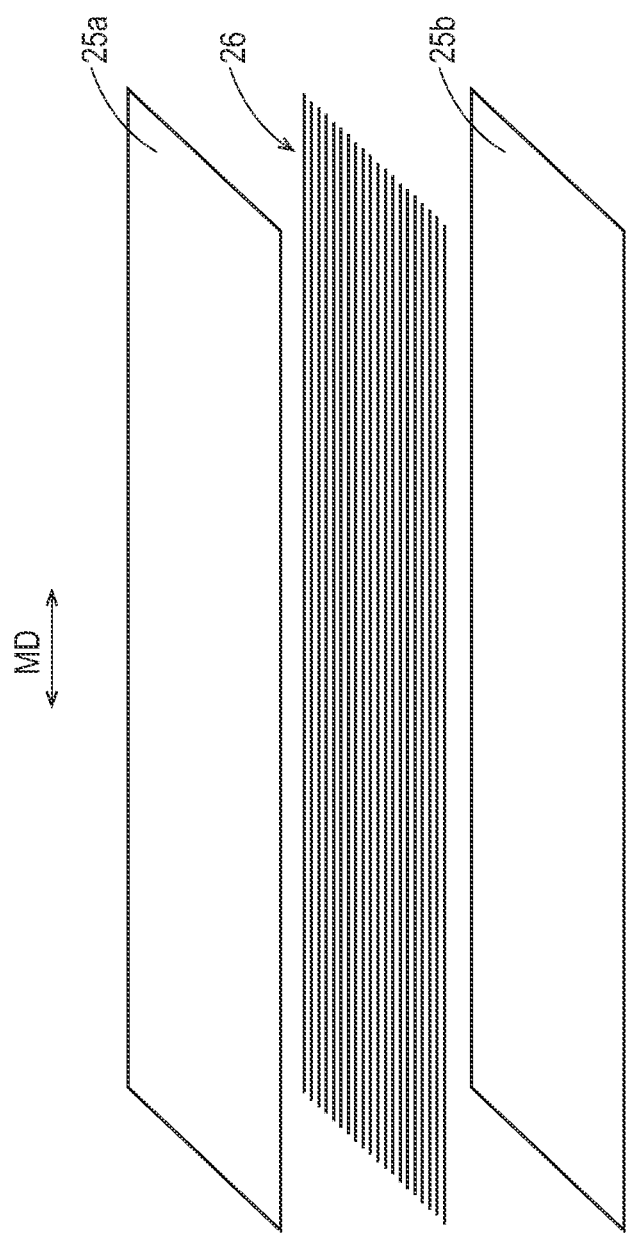
FIG. 3 is a schematic, exploded perspective view of components of a belt portion.
Figure 4:
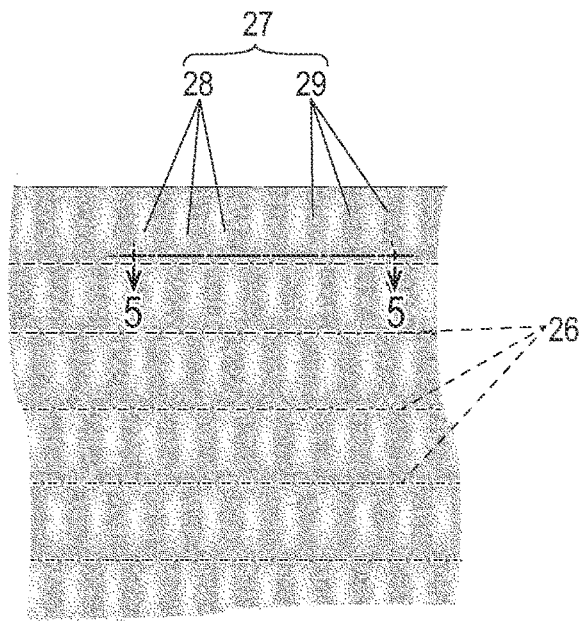
FIG. 4 is a schematic, close-up plan view of an area of a belt portion.
Figure 5:
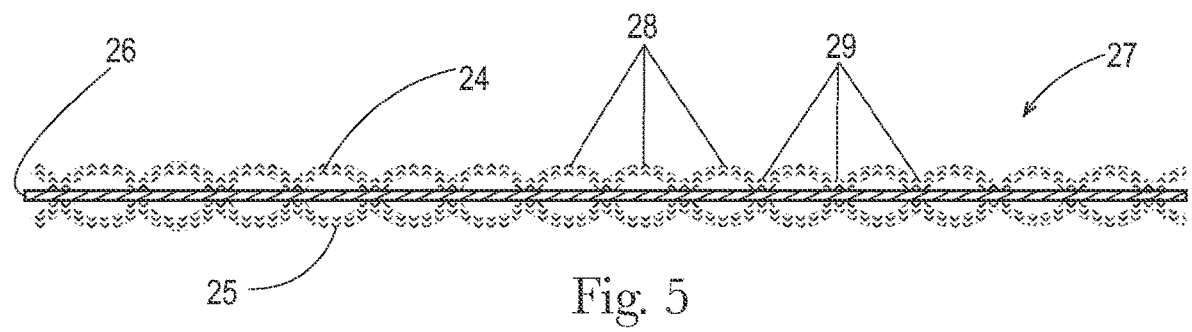
FIG. 5 is a schematic cross section of the area of the belt portion shown in FIG. 4.

Referring to FIGS. 3-5, one or both of front and rear belt portions 22, 23 may be formed of layers of nonwoven web 25a, 25b, which respectively form inner and outer layers. Suitable nonwoven web materials that may be useful in the present invention also include, but are not limited to spunbond, spunlaid, meltblown, spunmelt, solvent-spun, electrospun, carded, film fibrillated, melt-film fibrillated, air-laid, dry-laid, wet-laid staple fibers, and other nonwoven web materials formed in part or in whole of polymer fibers, as known in the art. The nonwoven web may be formed predominately of polymeric fibers. In some examples, suitable non-woven fiber materials may include, but are not limited to polymeric materials such as polyolefins, polyesters, polyamide, or specifically, polypropylene (PP), polyethylene (PE), poly-lactic acid (PLA), polyethylene terephthalate (PET) and/or blends thereof. In some examples, the fibers may be formed of PP/PE blends such as described in U.S. Pat. No. 5,266,392. Nonwoven fibers may be formed of, or may include as additives or modifiers, components such as aliphatic polyesters, thermoplastic polysaccharides, or other biopolymers. Further useful nonwovens, fiber compositions, formations of fibers and nonwovens and related methods are described in U.S. Pat. Nos.

6,645,569; 6,863,933; and 7,112,621; and in U.S. patent application Ser. Nos. 10/338,603; 10/338,610; and 13/005,237.

The individual fibers may be monocomponent or multicomponent. The multicomponent fibers may be bicomponent, such as in a core-and-sheath or side-by-side arrangement. Often, the individual components comprise polyolefins such as polypropylene or polyethylene, or their copolymers, polyesters, thermoplastic polysaccharides or other biopolymers.

According to one example, the nonwoven may comprise a material that provides good recovery when external pressure is applied and removed. Further, according to one example, the nonwoven may comprise a blend of different fibers selected, for example from the types of polymeric fibers described above. In some embodiments, at least a portion of the fibers may exhibit a spiral curl which has a helical shape. According to one example, the fibers may include bicomponent fibers, which are individual fibers each comprising different materials, usually a first and a second polymeric material. It is believed that the use of side-by-side bi-component fibers is beneficial for imparting a spiral curl to the fibers. Examples of potentially suitable curled or "crimped" bicomponent fibers and nonwovens formed from them are described in U.S. Pat. Nos. 5,382,400; 5,418,045; 5,707,468; 6,454,989, 6,632,386; 5,622,772 and 7,291,239. For purposes herein, use of a nonwoven formed of crimped bicomponent or multicomponent fibers such as, for example, described in the patents cited immediately above, may be desired as one both layers 25a, 25b used to form the belt portions, because they can feel particularly soft to the touch (for wearer comfort on the inside and aesthetically pleasing feel on the outside) and are generally quite pliable, making them easily drawn laterally at the lower rear leg edges as will be described below.

In order to enhance softness perceptions of the laminate, nonwovens may be treated by hydrojet impingement, which may also be known as hydroenhancement, hydroentanglement or hydroengorgement. Such nonwovens and processes are described in, for example, U.S. Pat. Nos. 6,632,385 and 6,803,103, and U.S. Pat. App. Pub. No. 2006/0057921.

Other examples of nonwoven web that may be useful in the present laminate may be an SMS web (spunbond-meltblown-spunbond web) made by Avgol Nonwovens LTD, Tel Aviv, Israel, under the designation XL-S70-26; a softband SSS (spunbond-spunbond-spunbond) web made by Pegas Nonwovens AS in Znojmo, Czech Republic, under the designation 18 XX 01 00 01 00 (where XX=the variable basis weight); an SSS web made by Gulsan Sentetik Dok San VE TIC AS, in Gaziantep, Turkey, under the designation SBXXFOYYY (where XX=the variable basis weight, and YYY=the variable cross direction width); an HESB (hydroenhanced spunbond) web made by First Quality Nonwovens Inc., in Hazelton, Pa., under the designation SEH2503XXX (where XXX=the variable cross direction width); and a bicomponent SS web. Inclusion of a meltblown layer (such as in an SMS web) may be desired because meltblown fibers, being much finer and of greater count per unit planar area, per unit basis weight, impart comparatively greater opacity to a web, per unit basis weight, than spunbond fibers. It may be desirable to utilize a nonwoven which includes a meltblown layer (such as an SMS web) for one or both of inner layer 25a and outer layer 25b, wherein the added opacity provides better concealment of the wearer's skin at the sides/hips.

Generally, the basis weight of a nonwoven impacts its thickness, pliability and tensile strength. For two respective nonwovens formed of otherwise identical types of fibers and through otherwise identical processes, with the only difference being basis weight, the nonwoven with the lesser basis weight will have a lower fiber count per unit planar area, and be the thinner and more pliable of the two. Conversely, the nonwoven with the greater basis weight will have a greater fiber count per unit planar area, and will be the thicker and stiffer of the two. Generally, the nonwoven with the greater basis weight, having a greater fiber count, will also likely have the greater tensile strength in the machine and cross directions.

A certain amount of machine and cross direction tensile strength is usually desired for processing; the nonwoven web must be able to sustain tensile loads imposed by processing equipment without tearing or exhibiting excessive deformation. Further, it may be desired that the nonwoven web portions of the belt structure impart a minimum lateral tensile strength to the belt at the limits of its ordinary stretch as in use (i.e., when all ruffles or rugosities 27 are pulled out). On the other hand, for purposes of forming a belt structure as described herein, a thinner and more pliable web may be desired for maximum breathability (to keep the wearer's skin beneath the belt structure relatively cool and dry) and comfortable fit. Maximum pliability is also desirable to facilitate lateral drawing back of the material at the lower rear leg edges as described below. Accordingly, selecting an appropriate basis weight involves finding an appropriate balance between these competing concerns. It is believed that the basis weight of the inner layer 25a is preferably selected to be from 7 gsm to 18 gsm, more preferably from 8 gsm to 15 gsm, and still more preferably from 9 gsm to 12 gsm. It is believed that the basis weight of the outer layer 25b is preferably selected to be from 10 gsm to 30 gsm, more preferably from 12 gsm to 25 gsm, and still more preferably from 14 gsm to 20 gsm. It will be understood that both layers 25a and 25b in combination add lateral tensile strength to the belt structure 23. The combined basis weight of both layers 25a and 25b (not including elastic strands) may be selected to be from 17 gsm to 48 gsm, more preferably from 20 gsm to 40 gsm, and still more preferably from 23 gsm to 32 gsm. The respective nonwoven materials used to form these layers may be selected to have equal or differing basis weights. It may be preferred to have the inner layer 25a to have lower basis weight than that outer layer 25b, to provide greater pliability of the ruffles or rugosities 27 next to the wearer's skin, while providing a thicker appearance on the outside.

In a particular example, inner layer 25a may be an SMS nonwoven as described herein having a basis weight from 7 gsm to 18 gsm, and outer layer 25b may be formed predominately of multicomponent or bicomponent, crimped fibers as described herein, having a basis weight from 17 gsm to 48 gsm.

Layers of nonwoven web 25a, 25b may sandwich one or more elastic members such as a plurality of strands 26 of an elastomeric material, such as an elastane (for example, LYCRA HYFIT fiber, a product of Invista, Wichita, Ks). Layers of nonwoven web 25a, 25b may be joined together about elastic strands 26 by adhesive deposited between the layers, by thermal bonds, by compression bonds, or by a combination thereof. In other examples, the one or more elastic members may be strips or a section of film formed of elastomeric material.

The elastomeric members can also be formed from various other materials, such as but not limited to, rubbers, styrene ethylbutylene styrene, styrene ethylene propylene styrene, styrene ethylene ethylene propylene styrene, styrene butadiene styrene, styrene isoprene styrene, polyolefin elastomers, elastomeric polyurethanes, and other elastomeric materials known in the art, and combinations thereof. In some embodiments, the elastic members can be extruded strand elastics with any number of strands (or filaments). The elastomeric members can have a decitex ranging from 50 to 2000, or any integer value for any decitex value in this range, or any range formed by any of these integer values. The elastomeric members may be in a form of film. Examples of films have been described extensively in prior patent applications (see, for example, U.S. Pat. App. Pub. No. 2010/0040826). The film may be created with a variety of resins combined in at least one of several sublayers, the latter providing different benefits to the film.

During manufacture of the belt structure, the elastic members such as elastic strands 26 may be pre-strained lengthwise by a desired amount as they are being incorporated into the belt structure. Upon subsequent relaxation of the belt, the elastic members such as elastic strands 26 will contract toward their unstrained lengths. This causes the layers of nonwoven material 25a, 25b to gather and form ruffles or rugosities 27 having ridges 28 and valleys 29 generally transverse to the lengths of the elastic strands 26, and extending in the z-direction.

It may be appreciated that the size(s) and shape(s) of the rugosities 27 will be affected, and may be manipulated, by design of the pattern of joined portions and/or bonding between the layers of nonwoven web 25a, 25b, with respect to each other and with respect to elastic strands 26. When joining and/or bonding is effected using adhesive deposited upon one or both layers 25a, 25b prior to lamination, the adhesive may be deposited in a pattern. Examples of methods for applying patterned deposits of adhesive to a nonwoven web substrate to enable manufacture of an elasticized laminate are described in U.S. Pat. No. 8,186,296. The pattern selected may be effected by design of a correspondingly designed roller. The pattern of adhesive to be applied may be designed to affect the size(s) and shape(s) of the rugosities 27. The layers 25a, 25b may be adhesively joined and/or bonded to each other at the locations of adhesive deposits, and remain unjoined or unbonded, or free, of each other at other locations, such that they may move and shift slightly relative each other as the laminate is moved and stretched, as during wear of the article. Similarly, when joining and/or bonding is effected using thermal calender bonding, the joining and/or bonding pattern may be designed to affect the size(s) and shapes of the rugosities 27.

In another example, to adhere the components of the belt laminate, the elastic strands 26 themselves may be individually coated with adhesive ("strand coated") prior to incorporation into the belt laminate. Upon subsequent lamination with layers 25a, 25b, this may be the primary mechanism of adherence or the layers 25a, 25b and the strands 26 to the laminate structure, at least in the majority of the planar surface area of the belt laminate in the areas laterally outside the outer perimeter 41 of the central chassis 30 (i.e., in the side/hip areas). This may provide advantages in that any pre-strain imparted to the elastic strands during manufacture will be evenly, fixedly distributed laterally to the layers 25a, 25b, promoting even formation and even lateral distribution and even sizing of rugosities 27 upon relaxation of the assembled belt structure or portions thereof. Additionally, since the belt laminate may be thus formed with layers 25a, 25b unadhered to the laminate except along the elastic strands 26, the layers 25a, 25b in the areas between the strands remain free to shift about and move independently of each other (including in the z-direction), providing added pliability, flexibility and loft to the belt laminate, which enhance wearer comfort and contribute to a luxurious look and feel. Strand coating in the lower half of the rear belt portion 23, or in the section of the rear belt portion disposed below the seam 24 and laterally outside the outer perimeter 41 of the central chassis 30, may be particularly advantageous because the above-referenced even distribution of elastic pre-strain, and pliability of the laminate, may better facilitate lateral drawing of the lower corner 21a of the rear belt portion 23 toward the central chassis 30, as will be described below. Thus, it may be preferred that layers 25a, 25b in the majority of the planar surface area of rear belt portion 23 laterally outside the outer perimeter 41 of the central chassis 30 and below seams 24 are adhered to the laminate along the elastic strands 26, but are unattached to the laminate structure along all or a majority of intervening areas 36, disposed laterally inward of seams 24, laterally outward of central chassis 30, between strands 26 and above lower lateral belt edge 18. Various coating methods and techniques, including strand coating methods and techniques, are shown for example in U.S. Pat. Nos. 5,340,648; 5,501,756; 5,507,909; 6,077,375; 6,200,635; 6,235,137; 6,361,634; 6,561,430; 6,520,237; 6,582,518; 6,610,161; 6,613,146, 6,652,693, 6,719,846 and 6,737,102. The adhesive used may be a hot-melt type adhesive having elasticity and flexibility making it suitable for attaching pre-strained elastic materials to substrates, such as OMNIMELT BLOCKS 22 H2401F, or ZEROCREEP brands such as AVANCÉ, available from Bostik, Inc., Wauwatosa, Wis.

Figure 6:
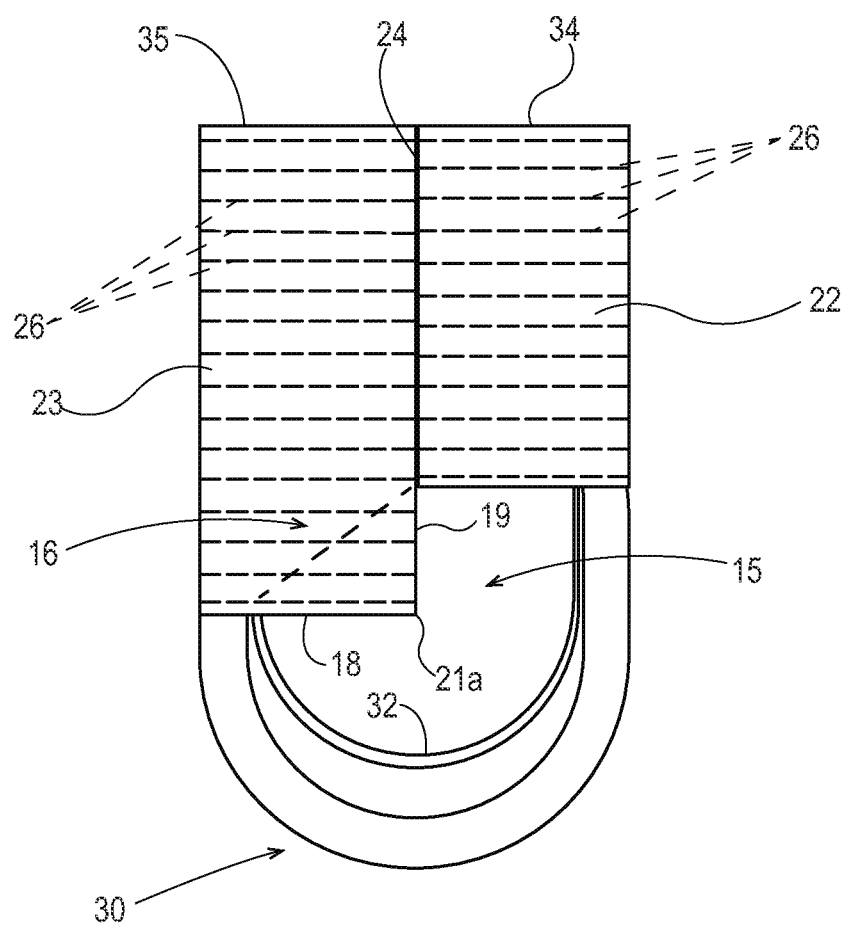
FIG. 6 is a schematic side view of a pant.

Referring to FIGS. 2 and 6, it can be seen that rear belt portion 23 may be made so as to be longer than front belt portion 22. This may be desired to provide leg opening 15 edges that are higher in the front of the pant than in the rear of the pant to more comfortably accommodate the wearer's forward bending of the legs at the hips (and reducing changes of rubbing or chafing of the wearer's skin at the front leg opening edges), while providing greater coverage of the wearer's buttocks at the rear. Considering FIG. 6, however, it can be seen that merely joining front 22 and rear 23 belt portions without some further modification will result in a leg opening edge that has a step profile to the rear of the side seam. When such a pant is worn, the areas of the rear belt portion 23 lying below lines of leg opening tension 16 (extending from the bottom extent of the side seam 24 to the point at which the rear belt portion 23 joins the chassis 30) including corner 21a may create an awkward or unsightly appearance. Portions of the material below lines of tension 16 may flip outward and/or curl, and thereby undesirably present a ragged, unfinished or haphazard appearance.

Figure 7A:
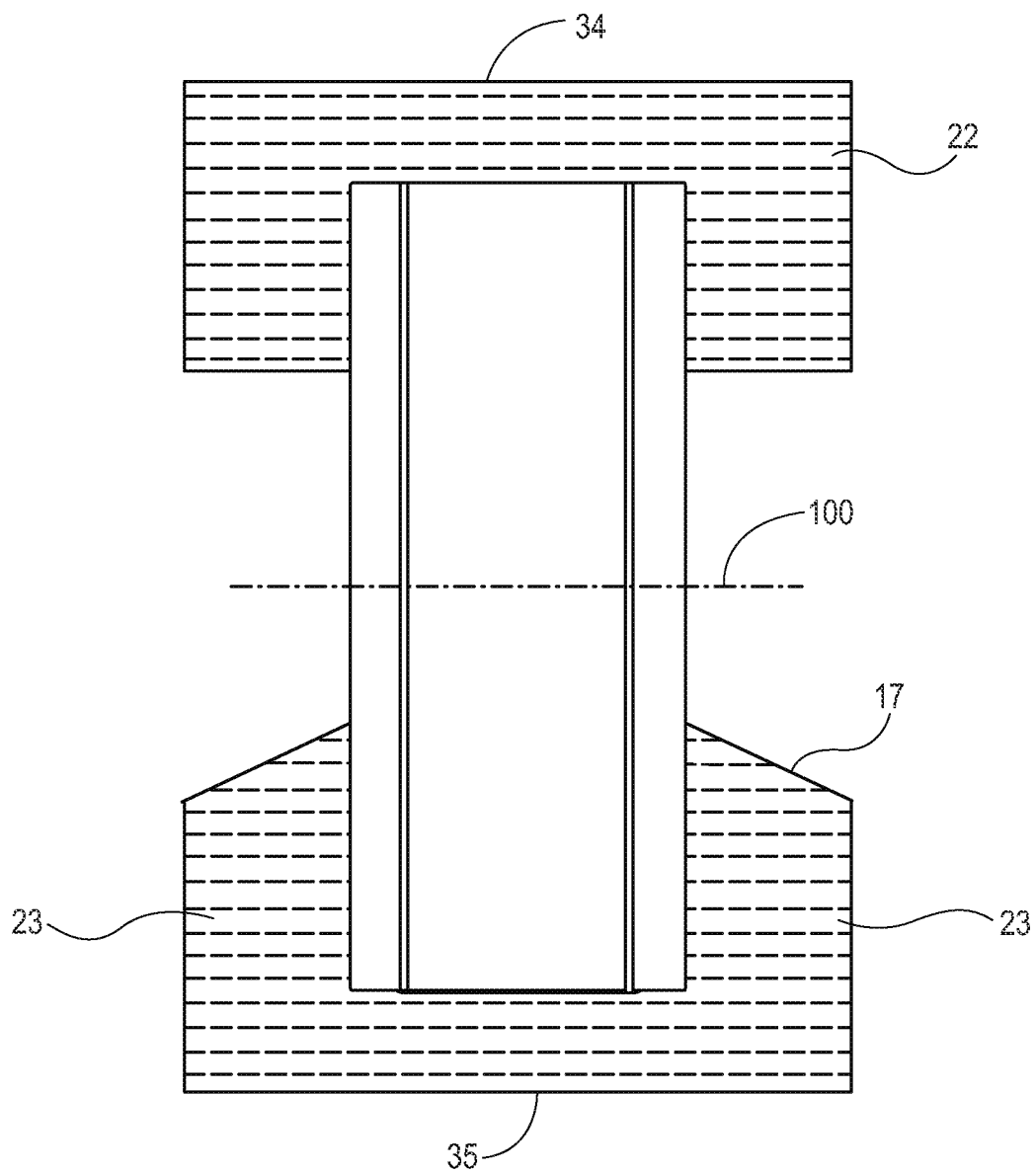
FIG. 7A is a schematic plan view of a balloon pant precursor structure, prior to joining of the front and rear belt portions at side seams, wearer-facing surfaces facing the viewer.
Figure 7B:
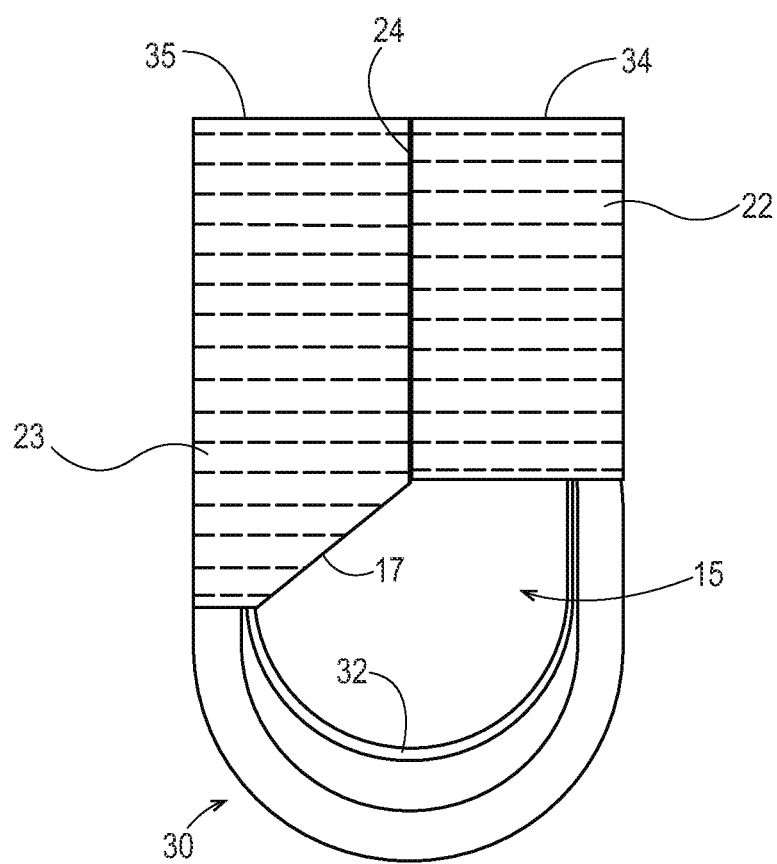
FIG. 7B is a schematic side view of a pant.

One solution to this problem is illustrated in FIGS. 7A and 7B. If, in manufacture of the pant, a section of the rear belt portion 23 is cut away along cut line 17 which may be approximately co-located along what would be the line of tension 16, the portions of the belt prone to flipping and/or curling are removed. The cut may also have any other suitable profile desired. It will be appreciated, however, that cutting away portions of materials in this manner creates a need for cutting equipment and a process, and generates cutoff scrap, which must be removed from the manufacturing line and plant environment, and either recycled or disposed of as waste. These necessities add cost and complexity to the manufacturing process.

Figure 8A:
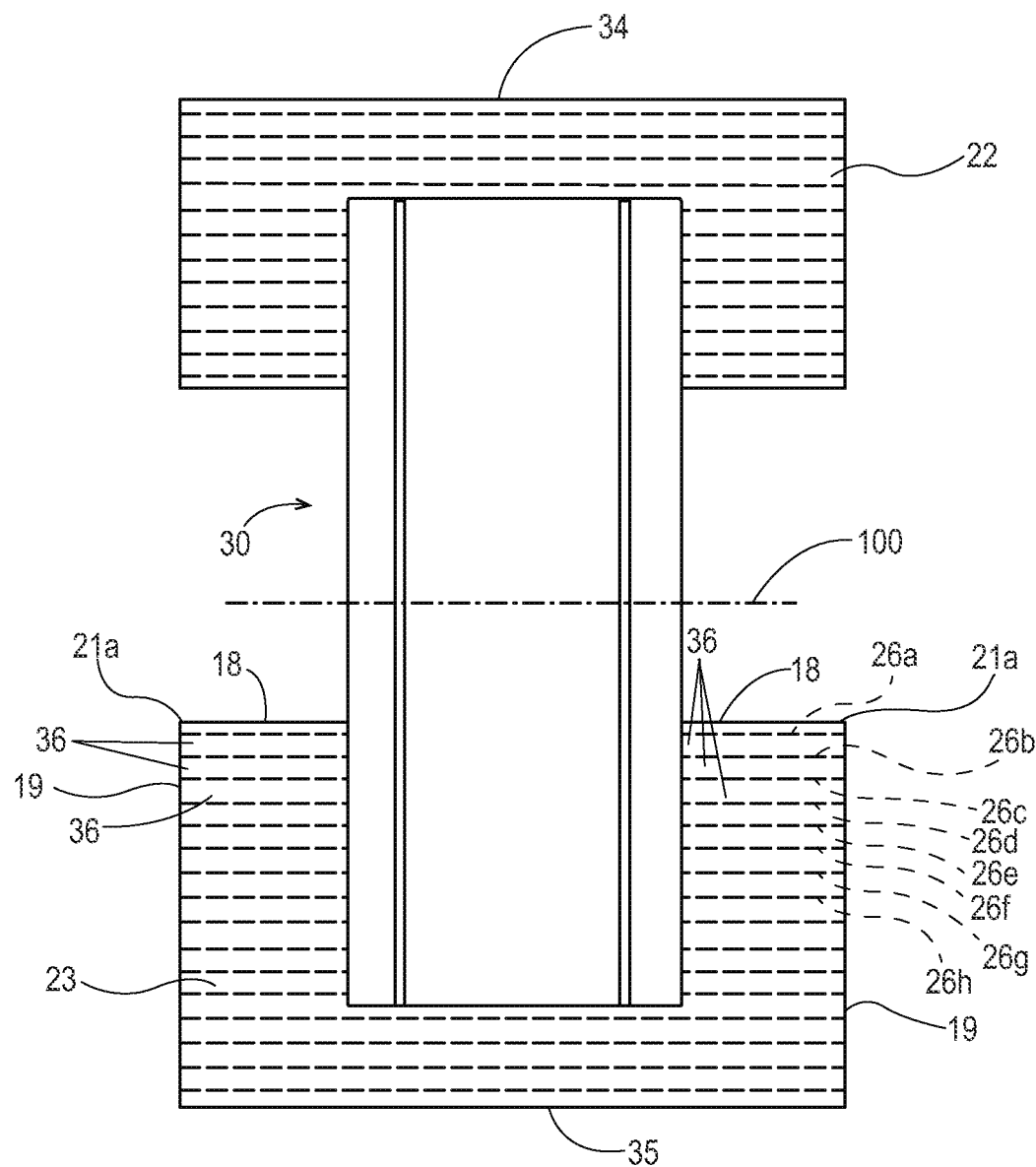
FIG. 8A is a schematic plan view of a balloon pant precursor structure, prior to joining of the front and rear belt portions at side seams, wearer-facing surfaces facing the viewer.
Figure 8B:
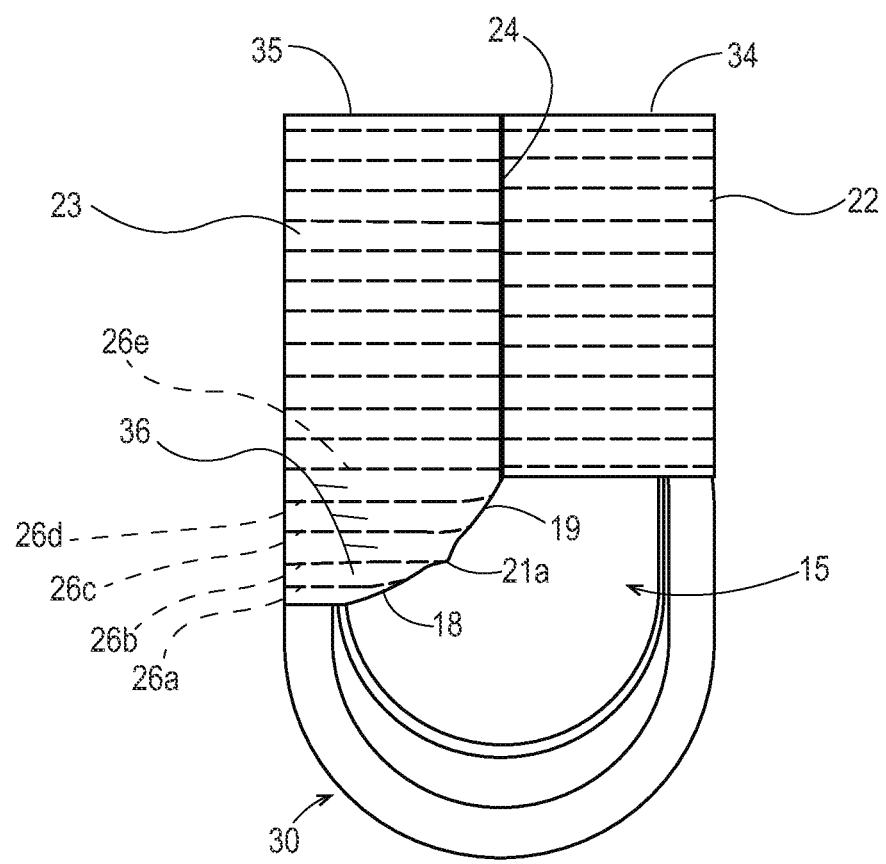
FIG. 8B is a schematic side view of a pant.
Figure 8C:
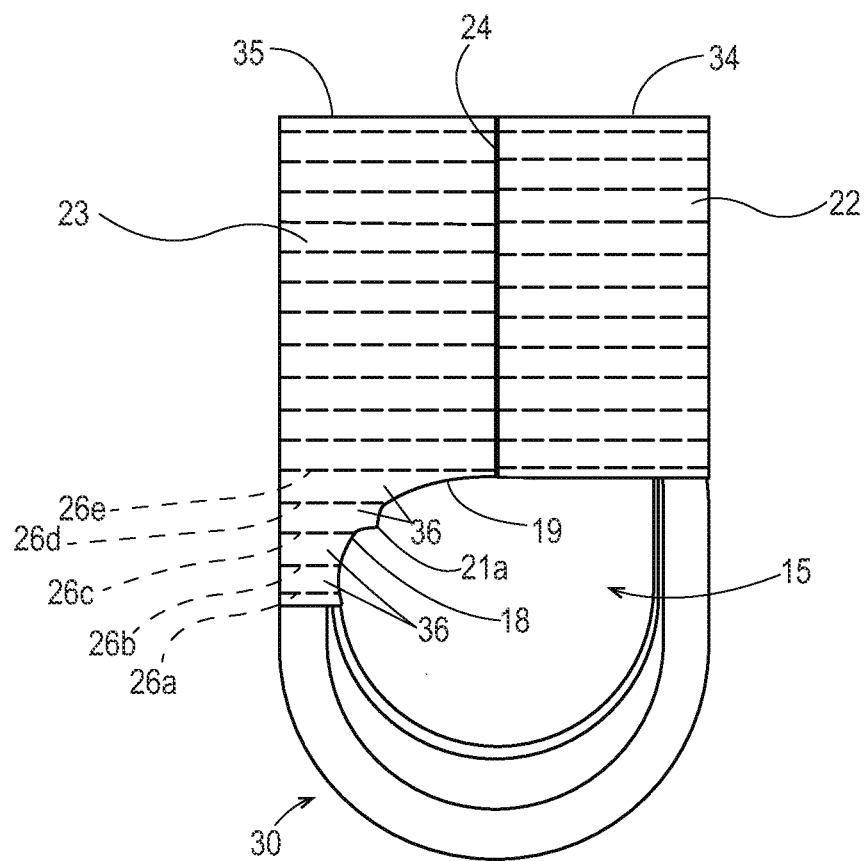
FIG. 8C is a schematic side view of a pant.

An alternative solution may be described with reference to FIGS. 8A-8C. Rather than elastic strands 26 of uniform modulus, decitex and/or extents of prestrain being incorporated into rear belt portion 23, elastic strands disposed on the lower area of rear belt portion 23, such as those disposed below seams 24, may have or may be imparted with different features that cause them to impart differing lateral contractive force(s), than the elastic strands above them.

In one example, one or more of the elastic strands disposed below a seam 24 may vary by one or more of the extent of prestrain, tensile modulus or decitex. One or more of comparatively greater prestrain, greater tensile modulus and/or greater decitex (same material) will cause an elastic strand to exert comparatively greater contractive force along its lateral length when elongated, as when the pant is worn. This greater contractive force will tend to cause the areas of the rear belt belt portion 23 about the elastic strand to be drawn laterally inwardly (toward the chassis 30) a comparatively greater distance, when the rear belt portion is allowed to partially or entirely relax laterally. The nonwoven layers 25a, 25b (see FIG. 5) will accommodate the greater lateral contraction by forming comparatively more numerous or larger rugosities 27 along/about the elastic strand.

It can be appreciated, then, that a lower group of elastic strands 26 in the rear belt portion, for example, a group disposed below a seam 24 (in the examples depicted in FIGS. 8A-8C, elastic strands 26a-26d) may be selected and/or pre-strained to impart grouped, or individualized, successively lesser or greater lateral contraction forces, about their lateral lengths, to the rear belt portion, to alter the profile assumed by the lower lateral belt edge 18 and side edge 19 lying below the seam 24 and laterally outside the outer perimeter 41 of central chassis 30. In a simple example, the lateral contractive force exhibited by the combination of the two lowermost elastic strands 26 in the rear belt portion (e.g., strands 26a and 26b in FIG. 8A) is greater than the lateral contractive force exhibited by the combination of the two uppermost elastic strands (e.g., strands 26c and 26d in FIG. 8A) disposed below seam 24, when the laminate is stretched to a uniform width. This may be accomplished by pre-straining the two lowermost strands by a combined greater amount than the uppermost strands, during manufacture. It may also be accomplished through use of strands having an average decitex greater for the two lowermost strands than for the two uppermost strands. For simplicity and reliability of manufacturing process, it may be preferred to use strands of differing decitex rather than to impart differing amounts of pre-strain/elongation to them during manufacture.

In another example, the amount of pre-strain of the lowermost elastic strand imparted during manufacture of the pant (e.g., strand 26a shown in FIG. 8A) is selected to be sufficiently high such that it cannot contract fully to its relaxed length upon completion of manufacture and subsequent relaxation of the belt structure, because sufficient material in the layers 25a, 25b is present to prevent such full contraction. This will ensure that tension is always present in the lowermost rear portion of the belt structure 23, which draws and holds corner 21a laterally inward toward the central chassis 30, even if the pant is worn by a relatively smaller wearer.

In another example, a lowermost strand in the rear belt portion (e.g., strand 26a shown in FIG. 8A) may be formed of the same elastomeric material but may have a decitex that is from 30% to 90%, more preferably from 40% to 80%, and still more preferably from 50% to 70%, greater than that of a highest elastic strand 26 disposed below seam 24 (e.g., strand 26d shown in FIG. 8A). In one particular example, one or more elastic strands disposed above the seam in the rear belt portion may be 940 dtex LYCRA strands, a first strand below the seam may be an 1100 dtex LYCRA strand, and a lowermost strand nearest the lower lateral edge may be a 1520 dtex LYCRA strand. (LYCRA strands are a product of Invista, Wichita, Kans.) If imparted with the same pre-strain during manufacture of the pant, these strands of differing decitex will impart differing laterally contractive forces in belt structure during wear, with the greater decitex strand imparting the greater laterally contractive force. It will be appreciated for this example, that the lowermost strand will impart the greatest laterally contractive force. The result will be that the lowermost strand will tend to cause lower corner 21a of the belt structure to be drawn laterally toward the center chassis 30, as suggested in FIG. 8B. The ruffles or rugosities 27 will be comparatively more numerous or larger in the areas of greater lateral contraction of the belt laminate.

The overall profile of the rear leg opening edge may be manipulated by varying the decitex and/or pre-strain of the elastic strands 26 disposed below the seam 24 in other ways.

In the example illustrated in FIG. 8B, lowest elastic strand 26a may be selected and/or prestrained to an extent that causes it to impose contractive force along its lateral length that is equal to or greater than any of elastic strands 26b, 26c, 26d, etc., which may tend to cause it to draw the areas of rear belt portion 23 lying along its lateral length toward the central chassis 30 by a distance equal to or greater than those areas disposed above strand 26a and below seam 24. Strands disposed above strand 26a (e.g., strands 26b, 26c, 26d) may be selected and/or prestrained to extents that cause them to impose successively less contractive force, causing them to draw areas of rear belt portion lying along their lateral lengths successively lesser distances toward the central chassis 30. As a result, lateral 18 and side 19 edges can be caused to define a generally convex profile, as suggested in FIG. 8B, when the pant is worn. With appropriate selection and/or extent of prestrain of the elastic strands disposed below the seam 24, the profile can be made fairly smoothed, with any discontinuity thereof at lower corner of rear belt portion 23 minimized.

In another example, lowest two elastic strands 26a, 26b may have a combined greatest decitex, and next lowest two elastic strands 26c, 26d may have a combined next greatest decitex that is less than the greatest decitex but greater than the decitex of strands disposed above the next lowest two elastic strands. In one even more particular example, the lowest two elastic strands and next lowest two elastic strands, respectively, may be formed of LYCRA, have a decitex of 1520 and 1100, respectively, and be prestrained at 290% when incorporated into the rear belt portion during manufacture thereof.

In another example illustrated in FIG. 8C, the elastic strands disposed below the seams 24 may be selected and/or prestrained so as to impart a differing profile to the lower rear leg opening edges formed by edges 18, 19, than that illustrated in FIG. 8B. In the example in FIG. 8C, one or more of the elastic strands (e.g., strands 26c, 26d) lying immediately below a seam 24 may be selected and/or prestrained so as to impart comparatively greater lateral contractive forces to the rear belt portion, than elastic strands below those (e.g., strands 26a, 26b). This may cause the rear belt portion to draw in laterally along a differing, generally convex profile, as suggested in FIG. 8C.

To maximize the rear edge profile and corner 21a smoothing effect, it may be desirable to limit the spacing between the lowermost elastic strands (e.g., strands 26a, 26b, 26c, 26d) in the rear belt portion. It may be particularly desirable that the spacing between the two lowermost strands (e.g., strands 26a, 26b) be no more than 10 mm, more preferably no more than 9.0 mm, even more preferably no more than 8.0 mm, and still more preferably no more than 7.0 mm. This helps ensure that the ruffles or rugosities 27 in the layers 25a, 25b proximate the lower edge 18, resulting from lateral contraction of the elastic strands, are controlled and kept relatively large in number, and consequently, relatively small in size.

In conjunction with the configuration of elastic strands described above, it may be desired that the lowermost elastic strand (e.g., strand 26a in FIGS. 8B and 8C) be disposed no more than 5.0 mm, more preferably no more than 4.0 mm, and even more preferably no more than 3.0 mm, from the lower lateral edge 18 of the rear belt portion, at least at lower corner 21a. This will minimize the amount of nonwoven material that is not controlled by an elastic strand, which may otherwise contribute to creating a ragged appearance at the leg opening edges—particularly at lower corner 21a.

Figure 9:
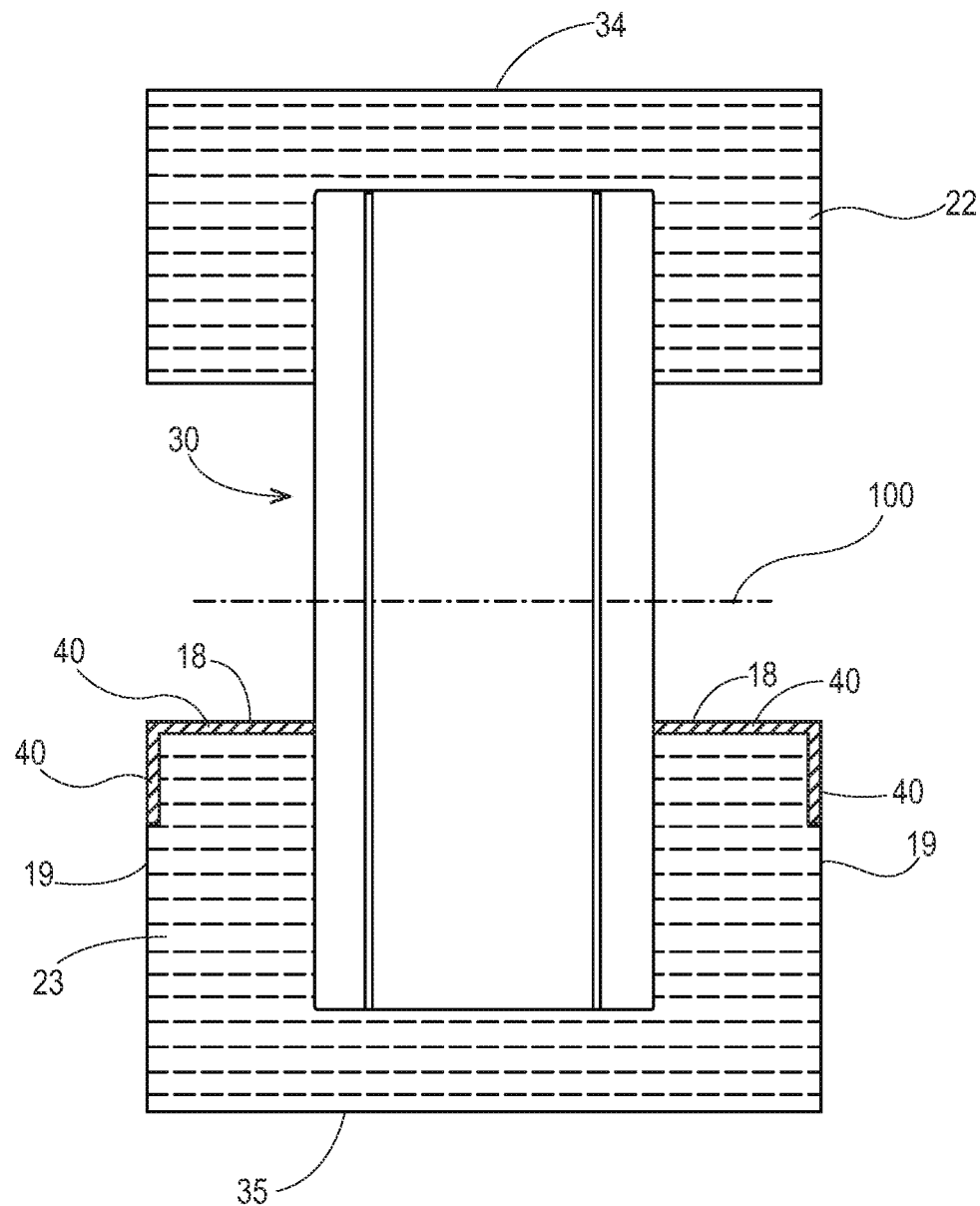
FIG. 9 is a schematic plan view of a balloon pant precursor structure, prior to joining of the front and rear belt portions at side seams, wearer-facing surfaces facing the viewer.

Referring to FIG. 9, also in conjunction with the configuration of elastic strands described above, it may be desired to impart bonding 40 between layers 25a, 25b along edges 18, 19, of rear belt portion 23. Such bonding may serve to prevent any separation of the layers along edges 18, 19 that may contribute to creating a ragged appearance, and may also help the rear belt portion more effectively draw inward laterally toward the central chassis 30, under the contractive force of the elastic strands below seams 24. Bonding 40 may be effected by mechanical/compression bonds as described in, for example, U.S. Pat. Nos. 4,854,984 and 4,919,738, by thermal bonds or welds, or by deposits of adhesive between layers 25a, 25b. As suggested in FIG. 9, such bonding may form a pattern along edges 18, 19. Such bonding may be supplemental to any bonding between layers 25a, 25b generally holding rear belt portion 23 together as a laminate structure.

Side seams 24 may be permanent or refastenable. Permanent seams are formed between the front belt portion and the rear belt portion by any bonding mechanism wherein the front and rear belt portions may not be forcibly separated without damage to one or both of the front and rear belt portions, or without any mechanism by which reattachment or refastening may be effected. Bonding forming permanent seams may include compression bonding, thermal bonding/welds or adhesive bonding. Refastenable seams are formed between the front belt portion and the rear belt portion by any mechanism configured to permit substantially non-destructive forcible separation of the front and rear belt portions, and subsequent reattachment or refastening along the same location. One example of such mechanism is a hook-and-loop fastening system, for example, a VELCRO fastening system. A suitably sized and shaped hooks component may be bonded to one of the front or rear belt portions along the longitudinal edges thereof, and a suitable sized and shapes loops component may be bonded to the other of the front or rear belt portions along the longitudinal edges thereof, in positions in which they may be brought together and engaged to form seams 24.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent pant comprising:
   a front belt portion,
   a rear belt portion, and
   a central chassis comprising an outer perimeter, a front region, a crotch region, a rear region, a topsheet, a backsheet and an absorbent core disposed between the topsheet and the backsheet, the central chassis being joined to the front belt portion in the front region, and being joined to the rear belt portion in the rear region;
   wherein the rear belt portion has a greater length than the front belt portion, and wherein the front belt portion is joined to the rear belt portion along respective left and right side seams;
   wherein a lower area of the rear belt portion comprises a lower lateral edge, lower side edges, and lower corners disposed between the lower lateral edge and the lower side edges, and wherein the lower area of the rear belt portion forms at least in part edges of left and right leg openings to the rear of the respective left and right-side seams, and wherein the rear belt portion comprises:
      first and second layers comprising first and second nonwoven web materials; and
      a plurality of longitudinally-spaced, pre-strained, laterally-oriented elastic strands sandwiched between the first and second layers and disposed below the side seams;
   wherein a first elastic strand of the plurality of elastic strands differs from a second elastic strand of the plurality of elastic strands disposed above the first elastic strand, by having greater pre-strain and/or greater tensile modulus;
   wherein the lower corners are disposed below the side seams and above the lower lateral edge when the pant is configured as worn;
   wherein an elastic strand positioned most proximal to the lower lateral edge is spaced no more than about 5 mm from the lower lateral edge; and
   wherein the first nonwoven web material has a first basis weight from 7 gsm to 18 gsm and the second nonwoven web material has a second basis weight from 10 gsm to 30 gsm.

2. The pant of claim 1 wherein a first group of the plurality of elastic strands differs from a second group of the plurality of elastic strands disposed above the first group, by having greater combined pre-strain.

3. The pant of claim 2 wherein the first group comprises at least 2 elastic strands.

4. The pant of claim 2 wherein a lowest elastic strand of the first group differs from a next lowest elastic strand of the first group, by having greater pre-strain.

5. The pant of claim 1 wherein a lowest of the plurality of elastic strands has greater pre-strain than all other elastic strands of the plurality of elastic strands.

6. The pant of claim 1 wherein the edges of the left and right leg openings formed by the rear belt portion define a generally convex profile when the pant is worn by a wearer.

7. The pant of claim 1 wherein each of the plurality of elastic strands has a pre-strain, and a lowest of the plurality of elastic strands does not contract to its unstrained length when the rear belt portion is relaxed.

8. The pant of claim 1 wherein a lowest of the plurality of elastic strands is spaced no more than 10 mm from a second lowest of the plurality of elastic strands.

9. The pant of claim 8 wherein the second lowest of the plurality of elastic strands is spaced no more than 10 mm from a third lowest of the plurality of elastic strands.

10. The pant of claim 1 wherein the side seams are permanent.

11. The pant of claim 1 wherein one or both of the side seams is refastenable.

12. The pant of claim 1 wherein the lower side edges of the rear belt portion disposed below the side seams comprise edge bonding between the first and second layers.

13. The pant of claim 1 wherein the lower lateral edge of the rear belt portion disposed laterally outside the outer perimeter of the central chassis comprise edge bonding between the first and second layers.

14. The pant of claim 1 wherein at least one of the first and second nonwoven web materials comprises meltblown fibers.

15. The pant of claim 1 wherein at least one of the first and second nonwoven web materials comprises bicomponent fibers.

16. The pant of claim 1 wherein at least one of the first and second nonwoven web materials comprises an SMS material.

17. The pant of claim 1 wherein the first layer is an inner layer, and wherein the first nonwoven web material comprises an SMS material.

18. The pant of claim 1 wherein one or more of the plurality of elastic strands comprises an adhesive coating.

19. The pant of claim 18 wherein the first and second layers are not adhered to each other over a majority of a planar surface area of the rear belt portion disposed below the side seams and laterally outside the outer perimeter of the central chassis.

20. A disposable absorbent pant comprising,
a front belt portion,
a rear belt portion, and
a central chassis comprising an outer perimeter, a front region, a crotch region, a rear region, a topsheet, a backsheet and an absorbent core disposed between the topsheet and the backsheet, the central chassis being joined to the front belt portion in the front region, and being joined to the rear belt portion in the rear region;
wherein the rear belt portion has a greater length than the front belt portion, and wherein the front belt portion is joined to the rear belt portion along respective left and right side seams;
wherein a lower area of the rear belt portion comprises a lower lateral edge, lower side edges, and lower corners disposed between the lower lateral edge and the lower side edges, and wherein the lower area of the rear belt portion forms, at least in part, edges of left and right leg openings to the rear of the respective left and right-side seams, and wherein the rear belt portion comprises:
    first and second layers comprising first and second nonwoven web materials; and
    a plurality of longitudinally-spaced, pre-strained, laterally-oriented elastic strands sandwiched between the first and second layers and disposed below the side seams;
wherein a first group of the plurality of elastic strands differs from a second group of the plurality of elastic strands disposed above the first group, by having greater combined pre-strain;
wherein the lower side edges of the rear belt define a generally convex profile from the side seams to the lower lateral edge, and wherein the lower corners are disposed below the side seams and above the lower lateral edge when the pant is configured as worn about a lower torso of a wearer;
wherein an elastic strand positioned most proximal to the lower lateral edge is spaced no more than 5 mm from the lower lateral edge, and wherein the elastic strand positioned most proximal to the lower lateral edge has greater pre-strain than all other elastic strands of the plurality of elastic strands; and
wherein the first nonwoven web material has a first basis weight from 7 gsm to 18 gsm and the second nonwoven web material has a second basis weight from 10 gsm to 30 gsm.

* * * * *